(12) United States Patent
Elsner

(10) Patent No.: US 10,507,085 B2
(45) Date of Patent: Dec. 17, 2019

(54) STRUCTURE ENABLING CONTINUOUS ANGULAR ADJUSTMENT FOR FIXING A SINGLE DENTAL DEVICE INTO AN IMPLANT

(71) Applicant: Edvin Elsner, Devecser (HU)

(72) Inventor: Edvin Elsner, Devecser (HU)

(73) Assignee: Elsner Global LLC, Charlestown, Nevis, WI (US)

( * ) Notice: Subject to any disclaimer, the term of this patent is extended or adjusted under 35 U.S.C. 154(b) by 27 days.

(21) Appl. No.: 15/568,286

(22) PCT Filed: Apr. 19, 2016

(86) PCT No.: PCT/HU2016/050014
§ 371 (c)(1),
(2) Date: Oct. 20, 2017

(87) PCT Pub. No.: WO2016/170376
PCT Pub. Date: Oct. 27, 2016

(65) Prior Publication Data
US 2018/0140390 A1     May 24, 2018

(30) Foreign Application Priority Data
Apr. 21, 2015  (HU) ..................................... 1500176

(51) Int. Cl.
*A61C 8/00* (2006.01)
(52) U.S. Cl.
CPC ............ *A61C 8/0053* (2013.01); *A61C 8/006* (2013.01)
(58) Field of Classification Search
CPC .............................. A61C 8/0053; A61C 8/006
USPC ................. 433/201.1, 74, 53, 172–176, 215; 523/120; 264/16–17; 623/16.11
See application file for complete search history.

(56) References Cited

U.S. PATENT DOCUMENTS

| 4,852,518 A | 6/1989 | Linkow et al. |
| 4,993,950 A * | 2/1991 | Mensor, Jr. .......... A61C 8/0048 433/173 |
| 5,009,596 A * | 4/1991 | Soderberg ............ A61C 8/0001 433/173 |
| 5,116,225 A | 5/1992 | Riera |
| | (Continued) | |

FOREIGN PATENT DOCUMENTS

| DE | 92 02 656 U1 | 4/1992 |
| EP | 0 580 945 A1 | 2/1994 |
| | (Continued) | |

*Primary Examiner* — Cris L. Rodriguez
*Assistant Examiner* — Mirayda A Aponte
(74) *Attorney, Agent, or Firm* — Jason D. Voight

(57) ABSTRACT

Structure enabling continuous angular adjustment for fixing a single dental device to an implant. The structure is formed from a ringwise tiltable threaded shank and a fixing unit for fixing the threaded shank to the implant. The fixing element is formed from an insertion piece and an intermediate piece. The lower end of threaded shank is placed between the end of the insertion piece and the upper end of the intermediate piece. A fixing nut is mounted on the threaded shank. The intermediate piece and the insertion piece are secured to each other by a joining element. The joining element is provided with lower corners and upper corners. A coupling body is installed on the joining element. A mould or the frame is fixed to the coupling body by the fixing nut.

3 Claims, 6 Drawing Sheets

(56) References Cited

U.S. PATENT DOCUMENTS

| | | | |
|---|---|---|---|
| 6,012,923 A * | 1/2000 | Bassett | A61C 8/005 |
| | | | 433/172 |
| 6,358,052 B1 | 3/2002 | Lustig et al. | |
| 2006/0024644 A1 | 2/2006 | Cohen | |
| 2012/0288827 A1 | 11/2012 | McBride et al. | |
| 2014/0162211 A1 | 6/2014 | Mullaly et al. | |
| 2015/0313690 A1 | 11/2015 | Elsner | |

FOREIGN PATENT DOCUMENTS

| | | | | |
|---|---|---|---|---|
| HU | WO 2014106761 A2 * | 7/2014 | ........... | A61C 8/0053 |
| HU | 229 980 B1 | 3/2015 | | |
| WO | 2008/138852 A1 | 11/2008 | | |

* cited by examiner

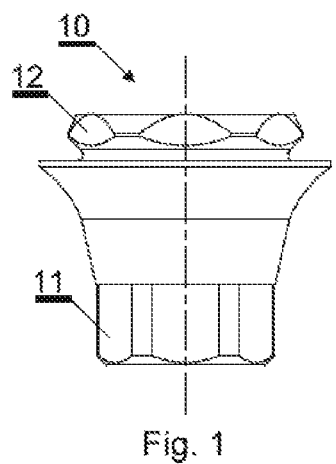
Fig. 1
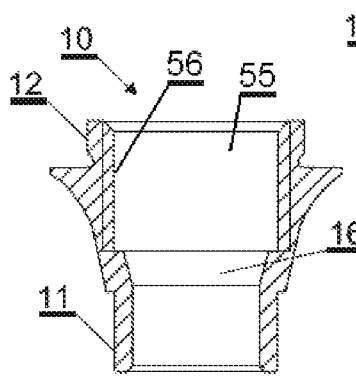
Fig. 2
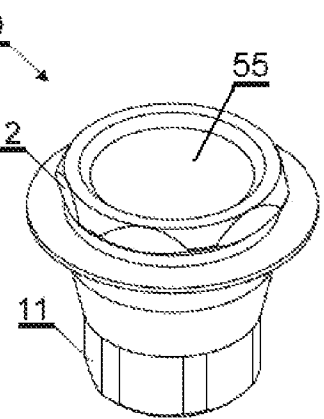
Fig. 3
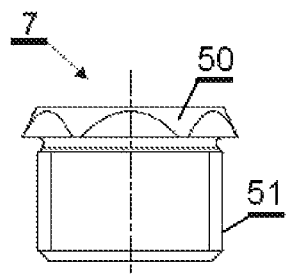
Fig. 4
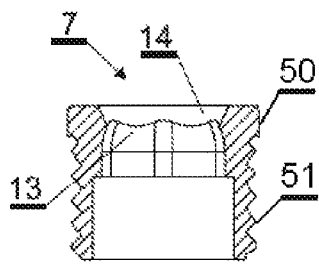
Fig. 5
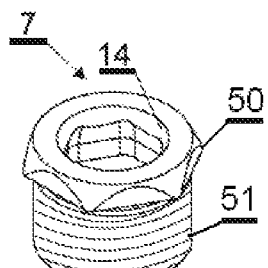
Fig. 6
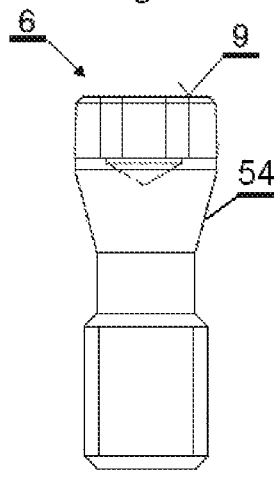
Fig. 7
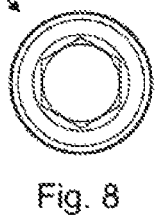
Fig. 8
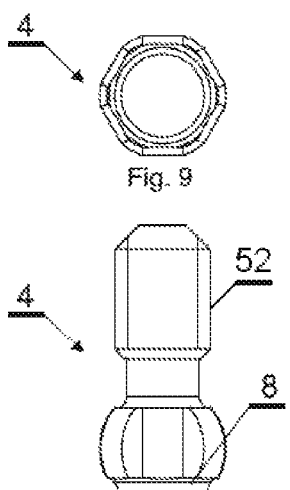
Fig. 9 / Fig. 10
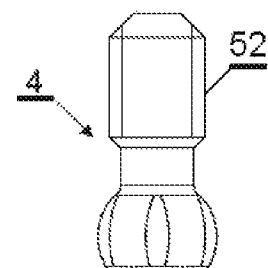
Fig. 11
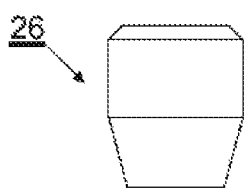
Fig. 12
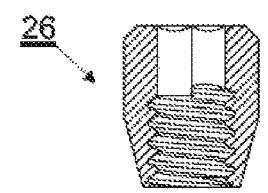
Fig. 13

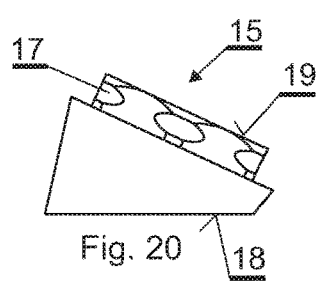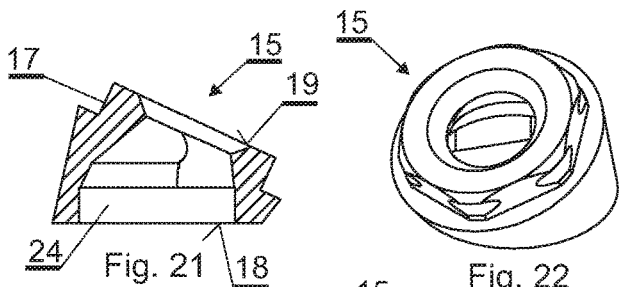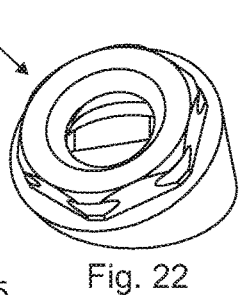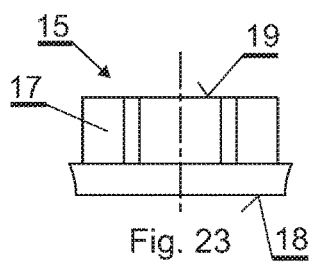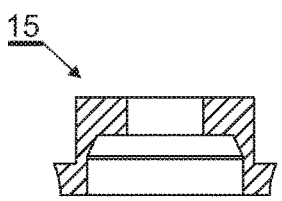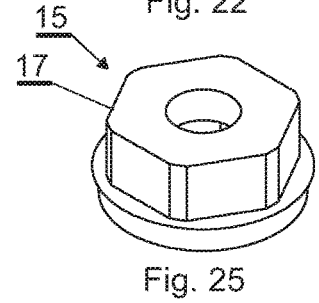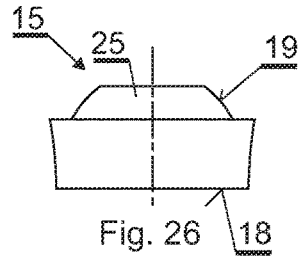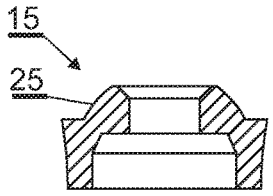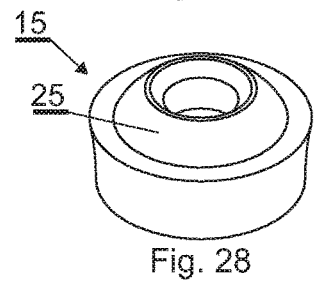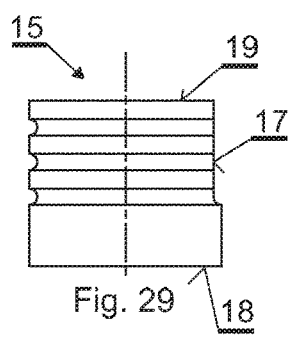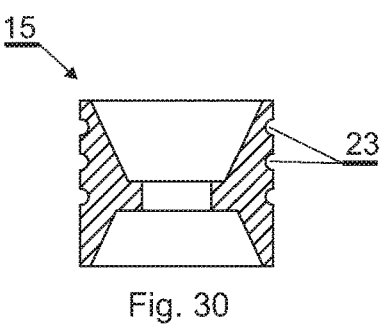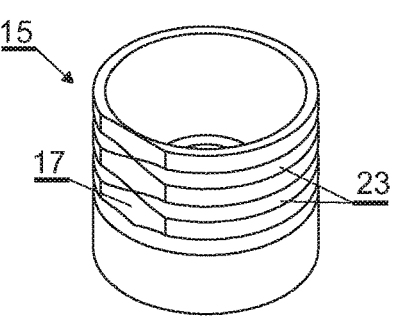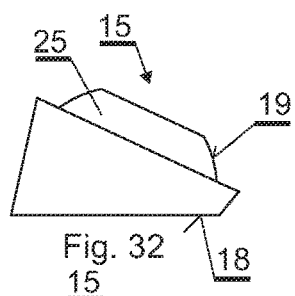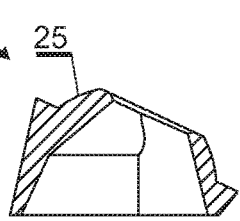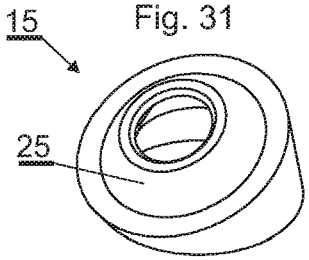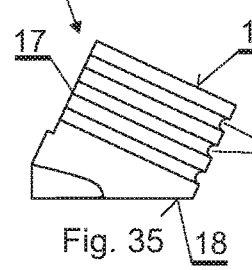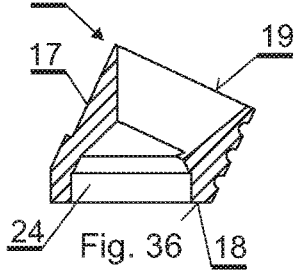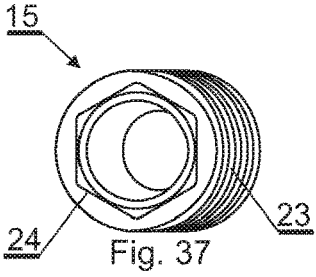

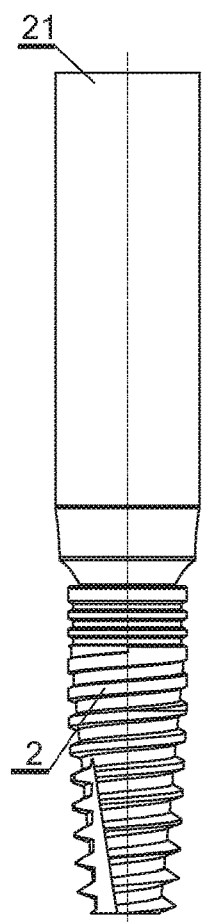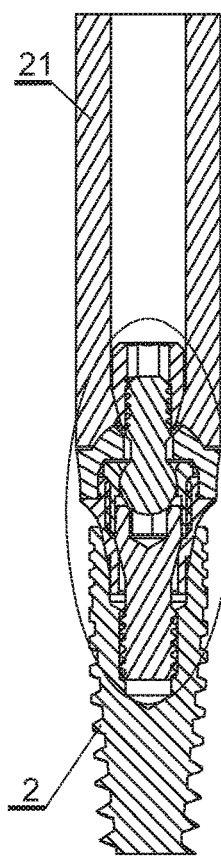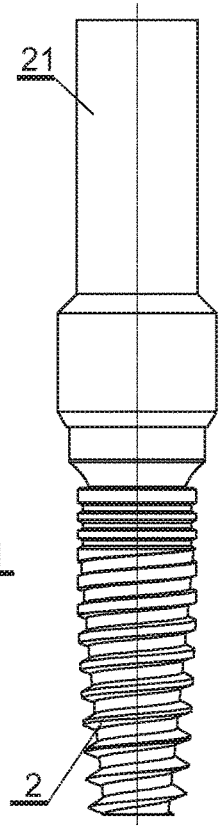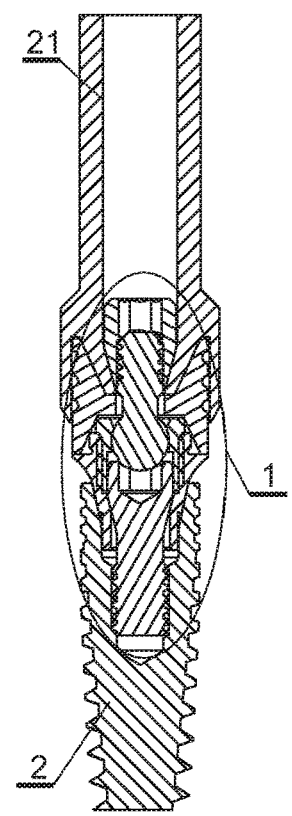
Fig. 48　　Fig. 49　　Fig. 50　　Fig. 51
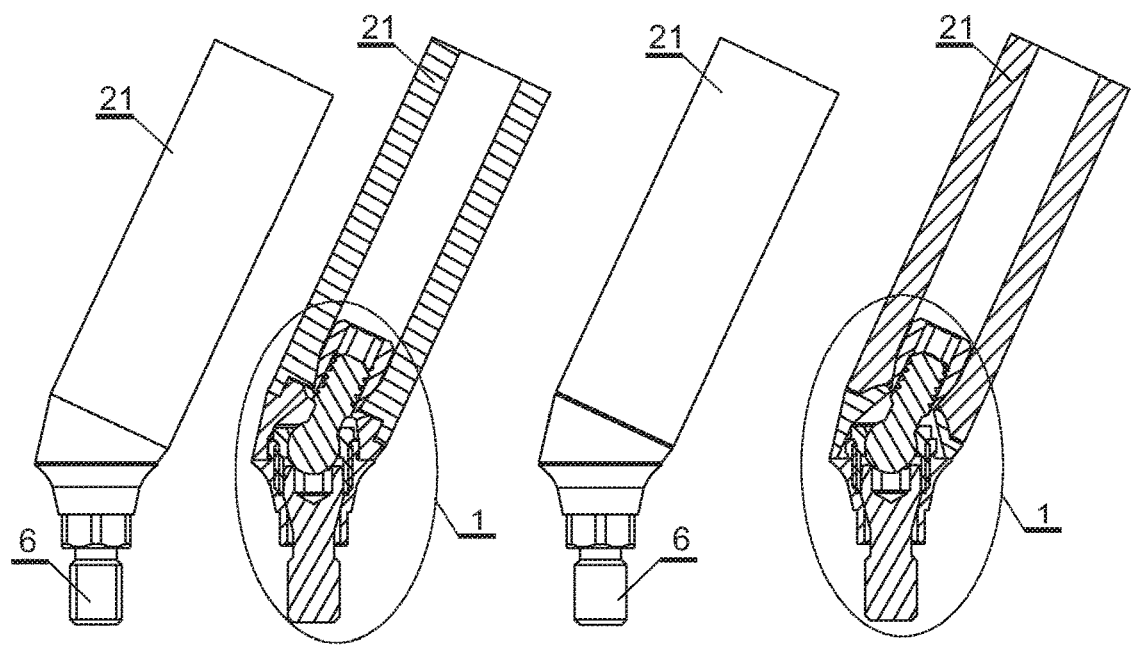
Fig. 52　　Fig. 53　　Fig. 54　　Fig. 55

STRUCTURE ENABLING CONTINUOUS ANGULAR ADJUSTMENT FOR FIXING A SINGLE DENTAL DEVICE INTO AN IMPLANT

This is the national stage of International Application PCT/HU2016/050014, filed Apr. 19, 2016.

The invention relates to a structure enabling continuous angle adjustment for fixing a single dental device into an implant. The structure is formed from a ringwise tiltable threaded shank projecting from the implant and a dental device fixing unit comprising a fixing element for fixing the threaded shank into the implant. The fixing element consists of an insertion piece and an intermediate piece provided with a bore-hole in which the threaded shank is led through in order to secure the insertion piece to the implant. The end of the insertion piece and the lower end of the threaded shank are attached to each other in a swivelable manner. The lower end of the threaded shank is positioned between the end of the insertion piece and the upper end of the intermediate piece. A fixing nut is installed on the threaded shank by means of which the frame of the dental device and/or the mould used for making the frame can be fixed.

BACKGROUND OF THE INVENTION

In case of dental prosthesis which are permanently fixed on an implant superstructure there is a growing requirement to employ bridges, crowns which are attached (screwed) in a releasable manner. Straight and/or angle deviation compensating superstructures which can be screwed into the implant by means of which dental devices can be built in the mouth are also applicable for implants where realization of the screw-joint is practically impossible because of the small internal cone angle (1-30°) since the included angle of the implants would be greater after they are built in. As the position of the implants is determined by the jaw-bone, it frequently happens that the divergence of the implants is even greater than 50°. That is often the case that a missing tooth is replaced by means of an implant and the dentist uses a system which cannot be used later as a 'bridge pier' fixed by a screw. In some cases in the course of time several type of implants are built in the patient's mouth which would present a problem of compatibility.

U.S. Pat. No. 5,116,225 describes an angulated abutment system for affixing a dental prosthesis to an anchor implanted in the jaw bone such that the dental prosthesis can be mounted axially offset from the axis of the implant. Two components of the abutment system are designed in such a manner to allow the dental prosthesis to be adjusted in small angles of rotation.

The aim of this solution was to make fixing of the superstructure possible from the side of the oral cavity, but the component parts used to this can be produced in a complicated manner. Though the channel is straight, forming the opening is very complicated because of the many intermediate elements.

International patent application WO 2008/138852 describes an adapter for a dental implant with a conical connection recess in its upper part. The adapter comprises a threaded part for connection with the dental implant and a conical main body corresponding to the conical connection recess of the implant, a tool grip portion allowing for attachment of the adapter to the implant by the aid of a tool.

The intermediate part used in this solution is an element provided with outer and inner threads which on the one hand is fixed to the implant and on the other hand the superstructure is fixed in it. Producing of this component part is very difficult and typically it is not used in these days as the superstructure is screwed in the implant directly. Possibly, a suitable interface is installed between the implant and the superstructure in order to ensure correct positioning of the superstructure.

These solutions can be used for adjusting a certain (0°, 15°, 20°, 25°) angle according to a predefined scale of the manufacturer.

U.S. Pat. No. 4,842,518 describes a screw-type implant which can be built in the jaw bone. In order to be able to position the implant at the most advantageous angle, angled abutments for supporting an artificial tooth structure or angularly adjustable abutments are provided.

Swivelling is prevented by frictional force as the fixing screw leans against the spherical shell of the ball and socket joint. The outer surface of the implant is not secured safely.

U.S. Pat. No. 6,358,052 teaches an implant system and method for effecting dental restoration. In a first step the position of the required dental prosthesis is determined, then in a second step this superstructure is worked out.

The implant is screwed in the jaw bone so that it can be adjusted as required to ensure the angle position by means of a ball joint. Then the positioning superstructure can be removed and the permanent superstructure can be produced according to the set position.

Patent application EP 0580945 describes an endo-osseous tooth implant for a fixed dental prosthesis having an essentially cylindrical round body of a metal for implantation in the jaw bone and a metal fastening head for a dental superstructure which can be firmly connected with an implant post. The metal implant post can be screwed into the inner bore which is open at its coronal end of the round body. The round body has on its coronal end a cylindrical annular recess provided with at least one basic body engaging element for reception of a cervical centering collar, provided with at least one spacer sleeve engaging element complementary to the basic body engaging element. The implant post has on its coronal end a partially spherical head which is flattened so as to be essentially plane toward the coronal side and whose diameter is larger than the diameter of an implant post stem located between a cervical threaded section and the partially spherical head.

Patent application EP1621156 also describes an implant system using a pivotal coupling between the implant and the abutment to permit precise angulation in all directions of the abutment.

However, in this solution using additional materials is required as swiveling can be prevented by gluing or welding.

Patent application WO2012/142517 A2 describes a dental implant system which can be used with a special implant family. In this solution the angle can also be adjusted by means of a ball-joint.

Swivelling is prevented by using a cup spring. However, if the spring gets worn out, the implant will be able to swivel and it is difficult to release the screw joint used for fixing. The surface of the upper end of the intermediate piece is ball-shaped on which the superstructure is placed, so it is not supported securely. At the same time it is difficult to block the way from bacteria's getting in.

In some cases the end of the threaded shank is ball-shaped which fits into a ball-shaped seat. When cup spring is used swiveling is prevented by the frictional force not by form fitting. In other cases the ball joint is provided on the upper end of the implant.

Patent application HU 229980 teaches a dental device fixing unit secured resiliently into implants enabling optional angular position adjustment. The fixing unit comprises a threaded shank tiltable in all direction projecting from the implant and a fixing element for securing the threaded shank to the implant. The fixing element consists of an insertion piece and an intermediate piece provided with a bore-hole in which the threaded shank is led through in order to secure the insertion piece to the implant. The end of the insertion piece and the inner end of the threaded shank are attached to each other in a swivelable manner. The inner end of the threaded shank is positioned between the end of the insertion piece and the upper end of the intermediate piece.

In this solution prevention of swiveling of the dental device fixing unit enabling optional angular position adjustment is not ensured by all means when a single tooth must be replaced. In spite of the fact that the insertion piece and the intermediate piece are secured to each other in unreleasable manner, the fixing unit is able to turn aside. If the intermediate piece is not circle symmetric, then the fixing unit cannot be screwed into the implant.

None of the known documents even the combination of them can give a solution for realizing the aim of the present invention.

The aim of the present invention is to improve the teachings of the international patent application WO 2014106761 based on Hungarian patent application HU 229980 in order to prevent the dental device from swiveling by all means, especially when a single dental device is needed to be fixed.

SUMMARY OF THE INVENTION

It has been realized that by installing an element between the implant and the intermediate piece so that one end of this element fits into the implant in form fitting manner while the other end of it joining to the frame is provided with surfaces which prevents the frame and the outer layer provided on it from swiveling, then the solution of HU 229980 can be applied reliably in case of replacing a single tooth. Accordingly, a structure enabling continuous angle adjustment for fixing a single dental device into an implant is provided. The structure is formed from a ringwise tiltable threaded shank projecting from the implant and a dental device fixing unit comprising a fixing element for fixing the threaded shank to the implant. The fixing element consists of an insertion piece and an intermediate piece provided with a bore-hole in which the threaded shank is led through in order to secure the insertion piece to the implant. The end of the insertion piece and the lower end of the threaded shank are attached to each other in a swivelable manner. The lower end of the threaded shank is positioned between the end of the insertion piece and the upper end of the intermediate piece. A fixing nut is installed on the threaded shank by means of which the frame of the dental device and/or the mould used for making the frame can be fixed.

The intermediate piece and the insertion piece are fixed to each other by means of a joining element placed in the implant. On the leg portion of the joining element facing the implant lower corners, while on its portion opposite the implant—i.e. at its end facing the intermediate piece—upper corners are formed. The upper corners are formed in a plane parallel to the plane of the lower corners and the number of the upper corners equals to the number of the lower corners. A coupling body provided with a bore-hole having a diameter greater than the outer diameter of the threaded shank is placed on the joining element. The lower surface and the upper surface of the coupling body are flat and the included angle between the two planes is 0-25°. In another case the lower surface of the coupling body is flat, the upper surface of it is a segment of a sphere and the included angle between the plane of the lower surface and the base plane of the segment of the sphere is 0-25°. The mould or frame is fixed to the coupling body by means of the fixing nut. The intermediate piece is secured into the joining element through threaded joint. Preferably, a portion of the outer superficies of the insertion piece is conical so that it can fit in the conical seat provided in the inner superficies of the joining element.

Preferred embodiments of the invention will be defined by the appended claims.

Detailed description of the invention will be given with reference to the accompanying drawings.

BRIEF DESCRIPTION OF THE DRAWINGS

FIGS. 1-3 show a possible embodiment of the joining element, namely:
FIG. 1 is the side view of the joining element;
FIG. 2 is the sectional side view of the joining element;
FIG. 3 is the perspective view of the joining element.
FIGS. 4-6 show a possible embodiment of the intermediate piece, namely:
FIG. 4 is the side view of the intermediate piece;
FIG. 5 is the sectional side view of the intermediate piece;
FIG. 6 is the perspective view of the intermediate piece.
FIG. 7 is the side view of the insertion piece;
FIG. 8 shows the insertion piece as viewed from above;
FIG. 9 shows the threaded shank of FIG. 10 as viewed from above;
FIG. 10 is the side view of the threaded shank;
FIG. 11 shows the side view of the threaded shank of FIG. 10 in a slightly rotated position;
FIG. 12 is the side view of the fixing nut;
FIG. 13 is the sectional side view of the fixing nut of FIG. 12;
FIGS. 16-37 show possible embodiments of the coupling body, namely:
FIG. 16 is the side view of a coupling body having parallel surfaces and not having corners;
FIG. 17 is the sectional side view of the coupling body of FIG. 16;
FIG. 18 is the side view of a coupling body having an angle α between the surfaces, where the coupling body does not have corners;
FIG. 19 is the sectional side view of the coupling body of FIG. 18;
FIG. 20 is the side view of a coupling body having an angle α between the surfaces and provided with corners;
FIG. 21 is the sectional side view of the coupling body of FIG. 20;
FIG. 22 is the perspective view of the coupling body of FIG. 20;
FIG. 23 is the side view of a coupling body having parallel surfaces and provided with corners;
FIG. 24 is the sectional side view of the coupling body of FIG. 23;
FIG. 25 is the perspective view of the coupling body of FIG. 23;
FIG. 26 is the side view of a coupling body having parallel surfaces, the upper being a segment of a sphere, where the coupling body does not have corners;

FIG. 27 is the sectional side view of the coupling body of FIG. 26;

FIG. 28 is the perspective view of the coupling body of FIG. 26;

FIG. 29 is the side view of a coupling body having parallel surfaces and corners;

FIG. 30 is the sectional side view of the coupling body of FIG. 29;

FIG. 31 is the perspective view of the coupling body of FIG. 29;

FIG. 32 is the side view of the coupling body having an angle α between the surfaces, the lower surface is flat, the upper surface is a segment of a sphere, and it does not have corners;

FIG. 33 is the sectional side view of the coupling body of FIG. 32;

FIG. 34 is the perspective view of the coupling body of FIG. 32;

FIG. 35 is the side view of a coupling body having an angle α between the surfaces and provided with corners;

FIG. 36 is the sectional side view of the coupling body of FIG. 35;

FIG. 37 is the perspective view of the coupling body of FIG. 35;

FIG. 38 is the bottom view of the mould shown in FIG. 39;

FIG. 39 shows a kind of mould viewed from the side;

FIG. 40 is the sectional view of the mould shown in FIG. 39;

FIG. 41 is the side view of another kind of mould;

FIG. 42 is the sectional view of the mould shown in FIG. 41;

FIG. 43 is the side view of another kind of mould;

FIG. 44 is the sectional view of the mould of FIG. 43;

FIG. 45 is the bottom view of the mould shown in FIG. 46, provided with matching surface;

FIG. 46 is the side view of another kind of mould provided with a matching surface;

FIG. 47 is the sectional view of the mould shown in FIG. 46;

FIG. 48 is the side view of the implant and a mould together with the structure in a straight assembly;

FIG. 49 is the sectional side view of the assembly shown in FIG. 48;

FIG. 50 is the side view of the implant and another kind of mould together with the structure in a straight assembly;

FIG. 51 is the sectional side view of the assembly shown in FIG. 50;

FIG. 52 is the side view of a mould as assembled and tilted by means of the structure at angle α, wherein swiveling is prevented by the corners and the surfaces;

FIG. 53 is the sectional side view of the assembly shown in FIG. 52;

FIG. 54 is the side view of another kind of mould as assembled and tilted by means of the structure at angle α, in this assembly prevention of swiveling is omitted in order to make building of the structure into a bridge possible;

FIG. 55 is the sectional view of the assembly shown in FIG. 54;

DETAILED DESCRIPTION OF THE INVENTION

Figure 14:
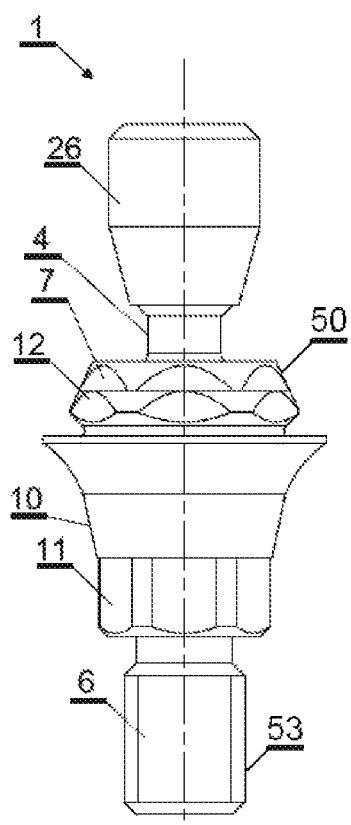
FIG. 14 is the side view of the structure.

In the description the terms 'prevention of swiveling' or 'swivelability' are used in relation to the coupling body and/or the mould, and they do not by any means refer to the joining element which must not swivel in the implant.

In the present invention, a structure 1 enabling continuous angle adjustment for fixing a single dental device into an implant is provided. The structure 1 is formed from a ringwise tiltable threaded shank 4 projecting from the implant 2 and a dental device fixing unit 3 comprising a fixing element 5 for fixing the threaded shank 4 to the implant 2. The fixing element 5 consists of an insertion piece 6 and an intermediate piece 7 provided with a bore-hole 14 in which the threaded shank 4 is led through in order to secure the insertion piece 6 to the implant 2. The end 9 of the insertion piece 6 and the lower end 8 of the threaded shank 4 are attached to each other in a swivelable manner. The lower end 8 of the threaded shank 4 is positioned between the end 9 of the insertion piece 6 and the upper end 13 of the intermediate piece 7. A fixing nut 26 is installed on the threaded shank 4 by means of which the frame of the dental device and/or the mould 21 used for making the frame can be fixed. The intermediate piece 7 and the insertion piece 6 are fixed to each other by means of a joining element 10 placed in the implant 2. On the leg portion of the joining element 10 facing the implant 2 lower corners 11 while on its portion opposite the implant 2 i.e. at its end facing the intermediate piece 7 upper corners 12 are formed. The upper corners 12 are formed in a plane parallel to the plane of the lower corners 11 and the number of the upper corners 12 equals to the number of the lower corners 11. A coupling body 15 provided with a bore-hole having a diameter greater than the outer diameter of the threaded shank 4 is placed on the joining element 10. The mould 21 or frame is fixed to the coupling body 15 by means of the fixing nut 26. The intermediate piece 7 is secured into the joining element 10 in a central hole 55 thereof through a threaded joint. Preferably, a portion of the outer superficies of the insertion piece 6 is conical so that it can fit in the conical seat 16 provided in the inner superficies of the joining element 10.

Figure 40:
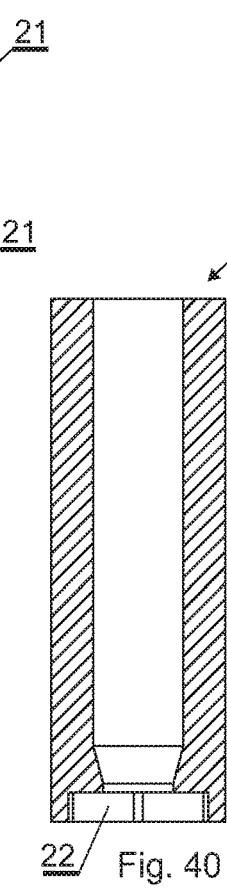
Figure 41:
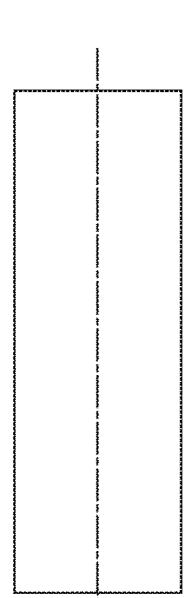
Figure 42:
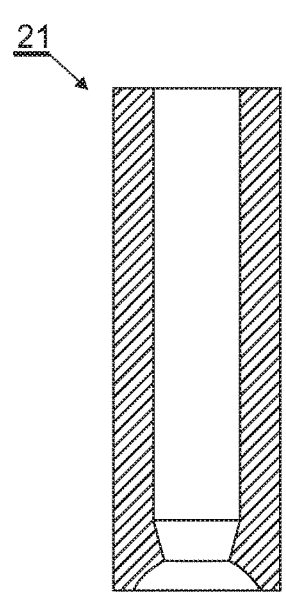
Figure 45:
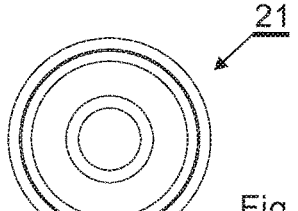
Figure 43:
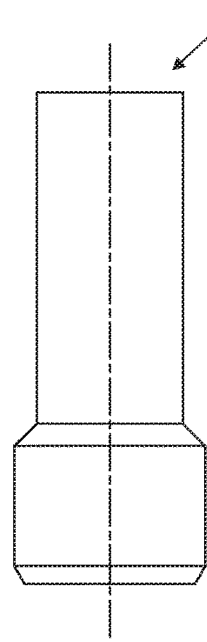
Figure 44:
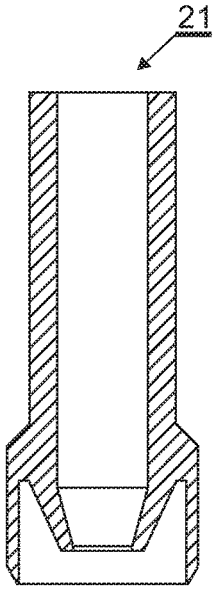
Figure 46:
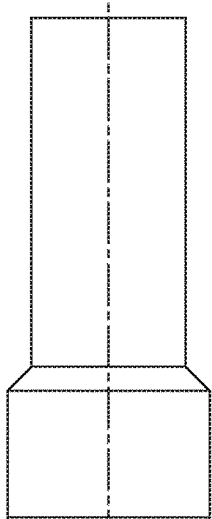
Figure 47:
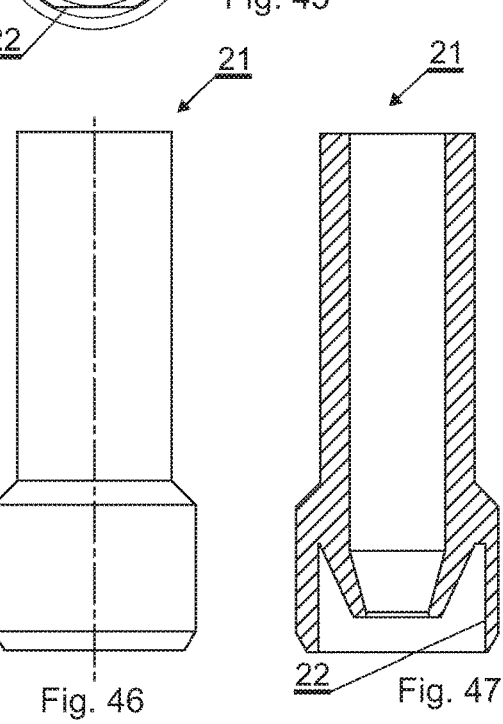
Figure 56:
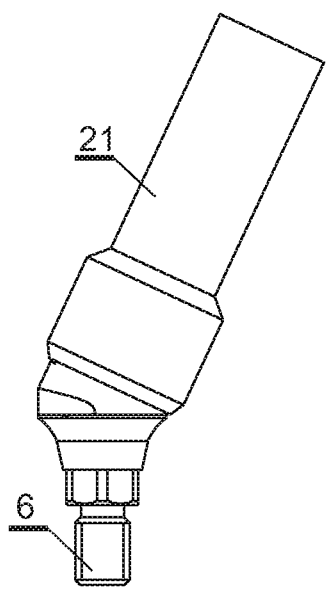
FIG. 56 is the side view of another kind of mould as assembled and tilted by means of the structure at angle α, wherein swiveling is prevented by the corners and the surfaces.

It is advantageous, principally when a single tooth is to be replaced—but also in case of making a bridge—if the coupling body 15 is installed on the joining element 10 and/or the intermediate piece 7 in form fitting manner. To this end coupling body 15 is provided with corners 17 so that swiveling of it is prevented (FIGS. 20, 29 and 35). On mould 21 and on the frame a surface 22 matching to corners 17 is formed (FIGS. 40 and 47). Further, coupling body 15 is provided with inner corners 24 matching to the upper corners 12 of joining element 10. The surface 22 of mould 21 facing to the fixing unit 3 fits to the upper surface 19 of coupling body 15. In this manner it is ensured that the direction of the additional superstructures relative to the joining element 10 is determined, fixed. That is, coupling body 15 is forced to have a determined position relative to joining element 10, and mould 21 is forced to have a determined position relative to coupling body 15.

Figure 19:
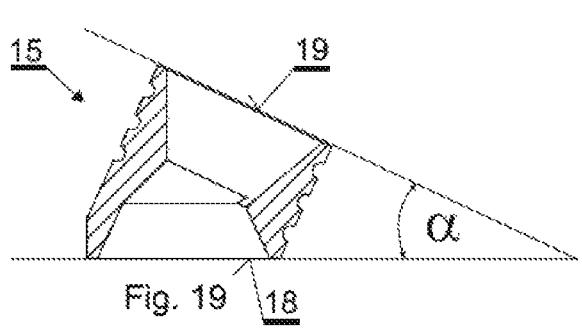
Figure 38:
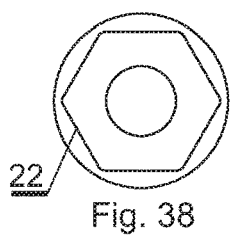
FIGS. 38-47 show possible embodiments of the mould, namely.
Figure 39:
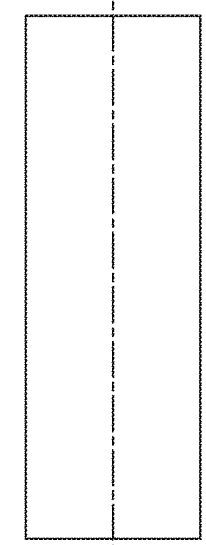

Usually it is sufficient if mould 21 is tilted by 5-5 degrees. Therefore the lower surface 18 and the upper surface 19 of coupling body 15 are formed as flat surfaces and the included angle α between them is 0-25° (FIG. 19).

In order to make further slight adjustment of mould 21 possible the lower surface 18 of the coupling body 15 is flat, the upper surface 19 of it is a segment of a sphere 25 (FIGS. 26-28 and 32-34). Also, in this case mould 21 can be tilted as required. That is, the included angle α between the plane of the lower surface 18 and the base plane of the segment of the sphere 25 is 0-25°.

Figure 15:
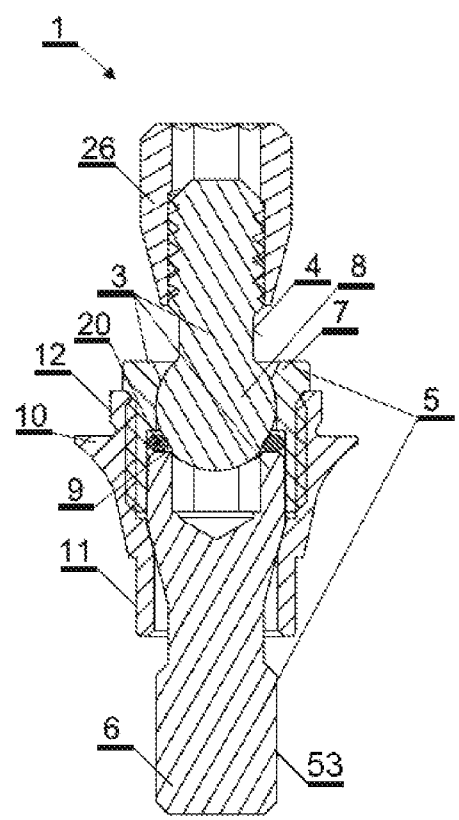
FIG. 15 is the sectional side view of the structure of FIG. 14.
Figure 16:
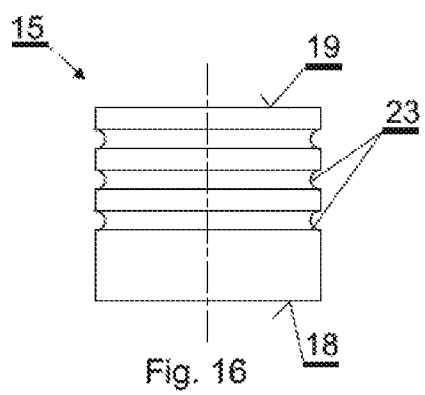
Figure 17:
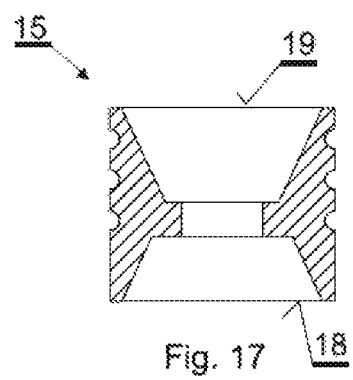
Figure 18:
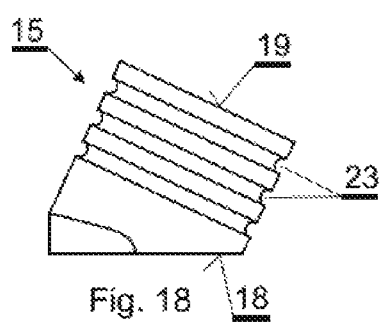

Preferably, a medical silicone ring 20 is placed between lower end 8 and end 9 in order to ensure the required position of the fixing element 5 during assembly (FIG. 15). After assembling silicone ring 20 has no function.

Advantageously, channels 23 are formed on the outer superficies of the coupling body 15 in order to ensure better fixing of mould 21. Channels 23 are filled with some adhesive.

With the present invention an improved fixing unit 3 of the one described in patent application HU 229980 and WO 2014106761 is provided. In the aforementioned documents the fixing unit 3 comprising threaded shank 4 (FIGS. 9-11) is installed in joining element 10 (FIGS. 1-3). Coupling body 15 is not shown in FIGS. 14 and 15. The advantage of the present invention is that incidental swivelling of fixing unit 3 after placing it into implant 2 is prevented by the structure 1 according to the present invention. It is very important when a single tooth must be replaced. To this, intermediate piece 7 (FIGS. 4-6) of the fixing element 5 of fixing unit 3 is provided with outer threads 51 at its lower end, and also with a coupling surface 50 configured to engage with a screwing tool at its opposite end (like the intermediate piece of WO 2014106761), and a portion 54 of the superficies of insertion piece 6 (FIGS. 7-8) is made cone-shaped. In the upper portion of the joining element 10 internal threads 56 matching to threaded portion 51 of the intermediate piece 7 are formed and under this threaded portion 56 a conical seat 16 is provided (FIG. 2). The threaded part 52 of shank 4 is lead out of fixing unit 3 through the bore-hole 14 of intermediate piece 7. The lower end 8 of the threaded shank 4 is installed between the upper end 13 of intermediate piece 7 and end 9 of insertion piece 6. Preferably, a medical silicone ring 20 is placed between the lower end 8 and end 9 in order to ensure the required position of the fixing element 5 during assembly. After assembling silicone ring 20 has no function. If it is important to prevent structure 1 from swivelling in implant 2 then lower corners 11 are formed on a portion of the outer superficies of joining element 10 in order to ensure matching between implant 2 and structure 1 in a form fitting manner (FIGS. 1-3). The lower corners can be shaped optionally, they can have the form of a hexagon or they can be formed as studs or grooves, etc. Further, by inserting a coupling body 15, mould 21 is secured to threaded shank 4 by means of fixing nut 26. For fixing the mould 21 (FIGS. 38-47) suitable coupling bodies 15 (FIGS. 16-37) are used installed on joining element 10. Swivelling of coupling bodies 15 is prevented by means of inner corners 24 matching to the upper corners 12 of joining element 10 and formed within coupling body 15. Structure 1 is fixed to mould 21 or to the frame formed with the mould (the latter is not shown in the Figures) by means of fixing nut 26 (FIGS. 12, 13). Swivelling of mould 21 is prevented by corners 17 provided on the outer surface of coupling body 15 (FIGS. 20-22 and 35-36) and by surface 22 formed on the inner surface of mould 21 (FIGS. 40, 47). Naturally, swivelling may be prevented in any other known manner.

In order to ensure that the bore-hole is not seen when the dental device is fixed, the threaded shank must be tilted in such a manner that the bore-hole of the fixing nut 26 faces the oral cavity. To properly adjust the angle of inclination of mould 21 the correct angle may be ensured by the coupling body 15. To this the lower surface 18 and upper surface 19 of the coupling body 15 are flat and the included angle α between the two planes is 0-25° (FIG. 19).

In order to make further slight adjustment of mould 21 possible the lower surface 18 of the coupling body 15 is flat, the upper surface 19 of it is a segment of a sphere 25 (FIGS. 26-28 and 32-34). Naturally, in this case also, mould 21 can be tilted as required. That is, the included angle α between the plane of the lower surface 18 and the base plane of the segment of the sphere 25 is 0-25°.

If needed, some adhesive may be applied in the channels 23 formed on the outer superficies of the coupling body 15 in order to glue mould 21 and coupling body 15 together.

Figure 57:
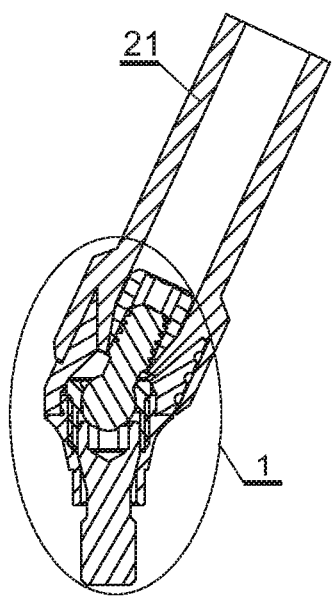
FIG. 57 is the sectional side view of the assembly shown in FIG. 56.
Figure 58:
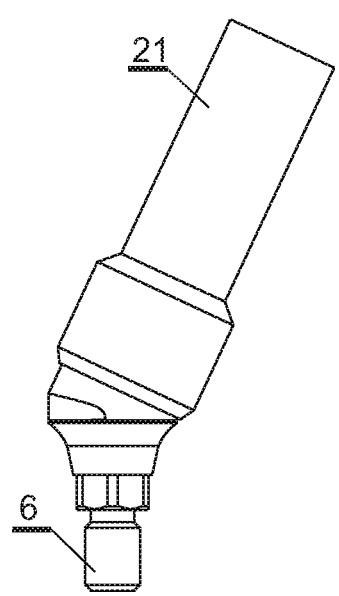
FIG. 58 is the side view of another kind of mould as assembled and tilted by means of the structure at angle α, in this assembly prevention of swiveling is omitted in order to make building of the structure into a bridge possible.
Figure 59:
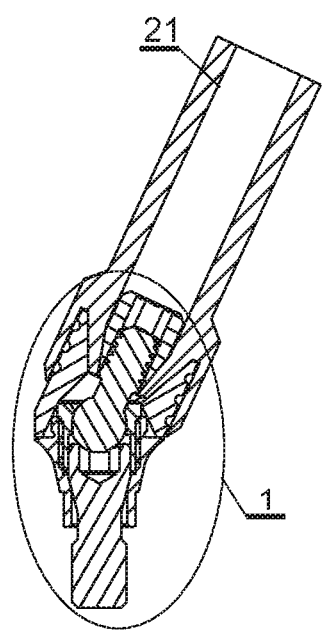
FIG. 59 is the sectional side view of the assembly shown in FIG. 58.

FIGS. 48-51 show the assembly of structure 1 and mould 21 placed in implant 2. In the Figures they are shown in straight position. However, in FIGS. 52-59 they can be seen in tilted position. In these Figures implant 2 is not shown. In FIGS. 53 and 57 solutions of the present invention for 'prevention of swiveling' are shown while the solutions shown in FIGS. 55 and 59 do not comprise 'prevention of swiveling'. Naturally, in each case the joining element 10 according to the invention is used and the respective coupling body is shown. In both solutions joining element 10 must ensure that fixing element 5 after installing it in implant 2 does not swivel. That is, 'prevention of swiveling' or 'swivelability' is used in relation to the superstructures built on fixing unit 3 and does not relate to the fixing element 5 installed in implant 2.

The advantage of the fixing unit according to the invention is that by making the threaded shank tiltable the dental devices can be fixed in the mouth so that their angle deviation relative to the direction of the implant can be compensated. The bore-holes of the screws are not perceptible to the eye as they are provided on a hidden surface of the dental device. The fixing unit according to the invention can be used with new implants as well as with implants installed earlier. Further, it can be used when a single tooth must be replaced or even in case of a fourteen-unit (full) bridge. The fixing unit cannot get unscrewed. It can be used to fix a dental device or crown comprising a curved bore-hole (described in an earlier patent application of the present inventors). The fixing unit of the present invention is a universal, continuously adjustable superstructure which ensures fixing without the possibility of swiveling. It can be used not only in case of bridges where prevention of swiveling is not reasoned but also for replacing a single, screwable unit.

The invention claimed is:

1. A fixing device for securing a dental device to a dental implant, the fixing device comprising:
    an intermediate piece having
       an intermediate piece central hole,
       at an intermediate piece first end, a coupling surface configured to engage with a screwing tool,
       a socket adjacent to said intermediate piece first end, and
       a threaded outer surface at an intermediate piece second end opposite to the intermediate piece first end;
    a shank having a threaded outer surface at a shank first end, a ball-like element at a shank second end opposite to the shank first end;

an insertion piece having an insertion piece first end for supporting the ball-like element of the shank, an insertion piece second end opposite to said first end of the insertion piece for engagement with a dental implant, and an outer conical coupling surface adjacent to the insertion piece first end; and a joining piece having a joining piece central hole for receiving the intermediate piece and the insertion piece, a first outer coupling surface located at a joining piece first end, where the first outer coupling surface at least in part has a cross-section adapted for a form-fitting engagement with a dental device in a specific rotational position, a threaded inner surface within said joining piece central hole and located at the joining piece first end, a second outer coupling surface located at a joining piece second end opposite to said joining piece first end having a cross-section adapted for a form-fitting engagement with a dental implant in a specific rotational position, and an inner conical seat;

wherein in an assembled state of the fixing device the socket of the intermediate piece and the insertion piece first end holds the ball-like element of the shank in a manner that a longitudinal axis of the shank is capable of tilting with respect to a longitudinal axis of the intermediate piece at any angle within a range of 0°-25°, the intermediate piece is secured to the joining piece so that the threaded outer surface of the intermediate piece engages with the threaded inner surface of the joining piece, the insertion piece is secured to the joining piece by a taper fit between the outer conical coupling surface of the insertion piece and the inner conical seat of the joining piece.

2. The fixing device of claim 1, wherein the second coupling surface of the joining piece has a hexagonal cross-section.

3. The fixing device of claim 1, wherein both the first and second outer coupling surfaces of the joining piece are defined by a plurality of corners, wherein the first outer coupling surface has the same number of corners as the second outer coupling surface.

* * * * *